B. L. DENNISON.

Machine for Making Cushions for Finger-Ring Boxes.

No. 6780 Reissued Dec. 7, 1875

Witnesses.
Sam'l M. Barton
A. E. Drinson

Inventor.
B. L. Dennison.
by his Attys.
C. D. Wright & Brown.

THE GRAPHIC CO. PHOTO-LITH. 39 & 41 PARK PLACE, N.Y.

UNITED STATES PATENT OFFICE.

BENJAMIN L. DENNISON, OF BRUNSWICK, MAINE.

IMPROVEMENT IN MACHINES FOR MAKING CUSHIONS FOR FINGER-RING BOXES.

Specification forming part of Letters Patent No. 161,493, dated March 30, 1875; reissue No. 6,780, dated December 7, 1875; application filed October 12, 1875.

*To all whom it may concern:*

Be it known that I, BENJAMIN L. DENNISON, of Brunswick, in the county of Cumberland and State of Maine, have invented a new and useful Improvement in the Art of Making Cushions for Finger-Ring Boxes, and a machine adapted to carry out my improved art in a good and practical manner; and I do hereby declare that the following is a full, clear, and exact description of said art and machine, that will enable others skilled in the art to which my invention appertains to practice, make, and use the same, reference being had to the accompanying drawings and to the letters of reference marked thereon, forming a part of this specification.

The drawings represent a machine which illustrates one good and practical manner of carrying out my improved art.

Figure 1:
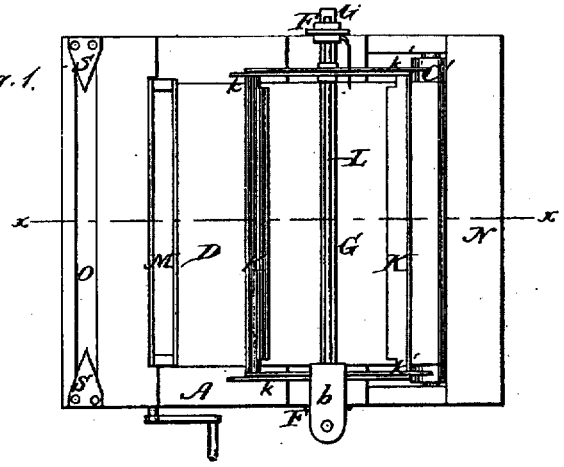
Figure 2:
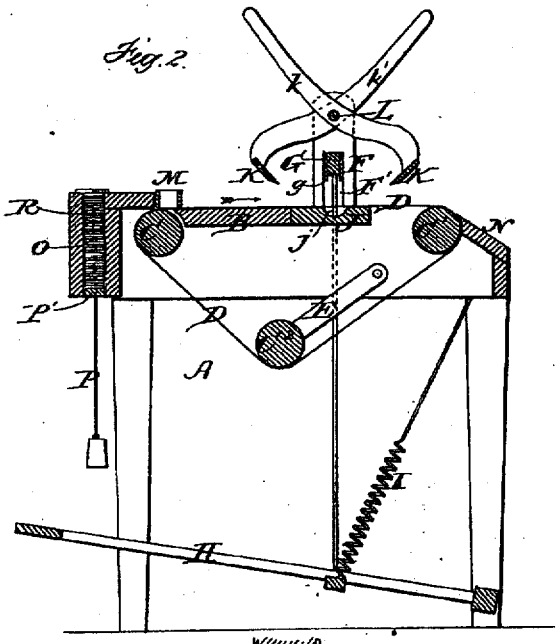
Figure 3:
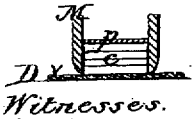
Figure 4:
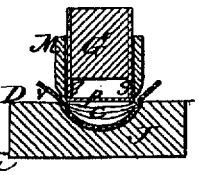
Figure 5:
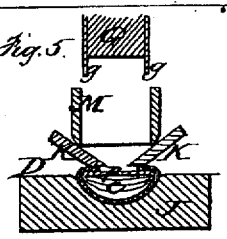

Figure 1 represents a top-plan view of my machine. Fig. 2 represents a section on the plane of line *x x*, Fig. 1. Figs. 3, 4, and 5 represent detail views, showing the positions of certain parts during different stages of the operation; and Figs. 6 and 7, sectional views, showing the completed cushion as it leaves the machine, and is applied in pairs to a ring-box.

My invention relates to the manufacture of the cushions which are inserted in pairs in finger-ring boxes, for the purpose of supporting a ring edgewise between them. These cushions are usually made in lengths sufficient to be cut up into a number of short cushions, and the following materials are employed in their manufacture, viz: a backing-strip of pasteboard, a facing or covering strip of velvet or other like material, and a filling strip or strips of cotton or other soft material interposed between the covering and backing. These parts are secured together by folding the edges of the covering-strip over the back of the backing-strip, and stitching said edges together or gluing them to the backing-strip, the covering-strip being wider than the backing and filling strips. These operations have been performed heretofore by hand, the two edges of the covering being secured gradually from end to end of the length when said edges are sewed together, and one edge at a time when glue is employed. Consequently, the production of the cushions has been slow and more expensive than is desirable in view of the large number of cushioned boxes used by the jewelry trade. In this hand manufacture it is difficult to secure the covering to the backing under a sufficient degree of tension to compress the filling, and enable the cushion to present a comparatively firm and smooth outer surface, this surface being flabby if the covering is not properly stretched or filled out.

My invention has for its object, first, to improve the art of making cushions for ring-boxes in such manner as to greatly facilitate the operation and improve the product; and, secondly, to provide a machine adapted to carry out my improved art in a good and practical manner.

My improved art of making cushions for finger-ring boxes consists, essentially, in piling the component parts of the cushion, viz., the backing, filling, and facing or covering, in the order in which they occur in the cushion, upon a bed or support, with the facing or covering strip at the bottom, and the backing at the top, applying pressure to the pile of material in such manner as to compress the filling between the covering and backing, coating the upper surface of the backing with glue, and folding both edges of the covering simultaneously over upon the adhesive surface of the backing while the filling is compressed. By this method I am enabled to compress the filling before securing the edges of the covering, and retain this compression until after said edges are secured, the subsequent expansion of the filling stretching the covering, and thus giving the cushion a comparatively firm and smooth outer surface.

My improved machine consists in a convenient combination of parts, adapted to carry out my improved art in a good and practical manner, all of which I will now proceed to describe.

In carrying out my improved art I prefer to employ a supporting-frame having a substantially-horizontal surface or bed and a substantially-horizontal pressure-bar located over said surface or bed and adapted to be depressed so as to bear downwardly on an object supported thereon. I place the component parts of the cushion—viz., the covering, the filling, and the backing—upon the bed in a pile, with the covering at the bottom and the backing at the top, the upper surface of the backing having a fresh coating of glue. The covering-strip is wider than the filling and backing, and its edges project on each side beyond the strips resting on it. I place the pile thus formed under the pressure-bar, in such relation to the latter that when it descends it shall bear upon the backing-strip along its entire length and press the strip downward, compressing the filling between the backing and covering. I then depress the pressure-bar and produce the last-described result; and then, with suitable folding devices, I turn both edges of the covering-strip simultaneously over upon the adhesive surface of the backing while the filling is compressed. The turned edges of the covering adhere readily to the fresh glue upon the backing, and when the pressure is removed the expansion of the filling stretches the covering and makes it tense, thus giving the outer surface of the cushion a smooth appearance and making the cushion comparatively firm.

By this method I am enabled to effect a saving of material over the ordinary hand method, for the reasons, first, that the edges of the covering are not required to overlap the backing so far, to be glued at both edges simultaneously, as to be sewed or glued at one edge at a time; and, secondly, that the filling material cannot be formed into so perfect a convex shape by hand. Consequently, to give the cushion the requisite thickness at the center, more filling material must be employed, while with my method the compression which the filling receives, the securing of both edges of the covering simultaneously while the filling is compressed, and the expansion of the filling after the pressure is removed, all tend to give the cushion its proper convex shape on the outer surface. Moreover, I have found, by experience, that the manipulation to which the cotton filling is subjected in hand manufacture tends to destroy its elasticity and thus impair its usefulness.

I have thus far described the essential features of my improvement in the art of making cushions. The machine I prefer to employ in connection therewith is represented in the drawings, in which A represents a suitable supporting-frame, having a substantially horizontal surface or table, B J. C C′ are parallel rollers extending across the frame A, each being journaled near the end of said frame, with its upper portion about flush with the upper surface of the table B J. D is an endless apron or carrier, which passes over the rollers C $C^1$ and table B J and under a third roller, $C^2$, which is journaled in pivoted arms E under the table B J, the weight of the roller resting on the apron and keeping it under the proper degree of tension. The apron D is of considerable width, as shown in Fig. 1, its width being preferably nearly equal to the length of the rollers C $C^1$. F F are vertical standards rising from opposite sides of the frame A, the apron D passing between them. The standards F have vertical slots $F^1$, which act as guides for the ends of a transverse horizontal bar, G, which slides up and down in said slots, its ends being connected by any suitable means with a treadle, H, by means of which it is depressed, a suitable spring, I, or its equivalent, being provided to raise the bar G, when the pressure on the treadle is released. The lower edge of the bar G is preferably provided with downwardly-projecting metallic lugs or flanges *g g*.

The part J of the table is preferably composed of a removable block extending across the table B between the standards F. The block J is provided with a concave groove, *j*, extending its entire length immediately under the sliding bar G, so that, as the latter descends, it will operate in connection with the groove, as will be hereinafter described. K K are transverse parallel swinging jaws, each attached to the ends of two pivoted levers, *k k k′ k′*, said levers being pivoted to a common fulcrum, L, which is preferably composed of a transverse rod extending from one standard F to the other, in the same vertical plane as the bar G and groove *j*. The jaws K are set at opposite angles on the ends of the levers *k k′*. When not in operation they are held apart, as shown in Figs. 1 and 2, by a pivoted block, *b*, interposed between the upper ends of the intersecting levers *k k′*; but when this block is removed the jaws fall, and their edges come together over the groove *j*, as shown in Fig. 5. M is a removable bottomless holder, composed of two parallel strips of sufficient length to extend across the apron D, said strips being connected at their ends and resting edgewise on the apron between the rollers C C′ in a position parallel with them.

The operation is as follows: A strip, *v*, of velvet, or other material suitable for the facing or covering of the cushion, of the desired length and width, is laid upon the horizontal portion of the apron D near the roller C, and parallel therewith, a suitable guide being employed for determining its proper position. The bottomless holder M is then placed upon the strip, as shown in Fig. 3, and in the holder is placed a strip, *c*, of cotton or other soft material of suitable thickness, its width and length being such as to enable it to be placed in the holder, which is narrower than the covering-strip *v*, the edges of the latter projecting on each side of the holder, as shown. A strip of pasteboard, *p*, or other stiff material, coated with fresh glue or other adhesive substance on its upper side, is then laid in the holder M on the filling *c*, the backing being of the same length and width as the filling. The roller C is then rotated by a crank at one of its ends in the necessary direction to carry the apron D in the direction of the arrow, Fig. 2, the holder M with its contents and the covering-strip *v* being thus advanced until they are directly over the groove *j* and under the bar G. The motion of the apron D is then arrested and the treadle H is depressed, forcing the bar G with its flanges *g g* down into the holder M, and pressing the backing *p*, filling *c*, and covering *v*, together with that portion of the apron on which the holder rests, downward into the groove *j*, the filling and backing being thus expelled from the holder, the filling being compressed, and the edges of the covering being caused to project diagonally upward, as shown in Fig. 4. The jaws K are next brought together, as shown in Fig. 5, their lower or inner edges catching the projecting edges of the covering *v*, and commencing to fold them over the edges of the backing *p*. The treadle H and bar G are released at this point, and raised by their spring, and the jaws are brought still nearer each other, maintaining the pressure on the backing, completing the folding of the edges of the covering, and pressing said edges upon the adhesive surface of the backing while the filling is compressed. The holder M, which is displaced by the jaws, as shown in Fig. 5, may then be returned to its former position, and prepared for a fresh operation, the jaws K being allowed meanwhile to remain on the cushion long enough to insure the necessary adhesion of the turned edges of the cover to the backing.

When the holder is prepared for a repetition of the above-described operation, the jaws are raised and the apron set in motion, carrying the holder toward its stopping-point, and, at the same time, carrying the cushion just completed to an inclined board, N, at the rear end of the frame, from whence it rolls into a suitable receptacle.

Stops *y y* may be provided, projecting over the apron D, and adapted to stop the holder M at the proper point under the pressure-bar.

Figure 6:
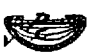
Figure 7:
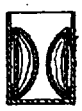

It will be seen, from the foregoing, that a cushion of any desired length can be made, this length being adapted to be cut up into sections for use, each section being a complete cushion, as shown in Fig. 6, and ready for insertion into a box, as shown in Fig. 7.

The concave form of the groove *j* molds the outer surface of the cushion, and gives it the necessary convexity; and, as the covering is secured to the backing while the filling is compressed, the cushion has a shape imparted to it which it is not liable to lose. The flanges *g* of the pressure-bar G projecting below the latter, their narrow edges are the only parts that come in contact with the glued surface of the backing *p*. Consequently, they do not interfere materially with the fresh adhesive material.

I prefer to employ a transverse receptacle, O, at the front end of the frame A for the purpose of holding a quantity of the backing-strips *p*. This receptacle has a bottom, P′, adapted to slide vertically, and connected to weighted cords P, passing over pulleys R in the ends of the receptacle. By this device the strips are fed upwardly as fast as they are used, and the upper surface of each of them may be coated with glue before it is taken from the receptacle.

S S are points or stops projecting inwardly from each end of the receptacle, and bearing upon the ends of the uppermost strip therein, to prevent the strips from being forced entirely out by the weighted bottom.

I do not desire to limit myself to the employment of the apron or carrier, the bottomless holder, and the grooved block J, as the operation of making the cushion can be performed without these parts.

I claim as my invention—

1. The described improvement in the art of making cushions for finger-ring boxes, which consists in the process of piling the component parts of the cushion upon a bed or support, with the covering-strip at the bottom, and the backing-strip at the top, of the pile, coating the exposed surface of the backing with glue or other adhesive material, applying pressure to the backing in such manner as to compress the filling between the covering and backing, and folding both edges of the covering-strip simultaneously over upon the adhesive surface of the backing while the filling is compressed, substantially as and for the purpose specified.

2. In a machine for making cushions for finger-ring boxes, the combination of a supporting bed or table, a substantially horizontal pressure-bar, adapted to press upon a pile composed of layers of material supported on said bed or table, and suitable folding devices, whereby the projecting edges of the lower strip or layer of material are folded over upon the upper surface of the upper strip or layer of material while said pile is compressed, all constructed and arranged substantially as and for the purpose specified.

3. The combination of a supporting bed or table, a substantially horizontal pressure-bar, a removable bottomless holder, and a pair of swinging jaws, all substantially as and for the purposes specified.

4. An endless apron or carrier, in combination with a supporting bed or table, a removable bottomless holder, and suitable compressing and folding devices, substantially as described, for the purpose specified.

5. A supporting bed or table having a groove, *j*, combined with a removable bottomless holder, a pressure-bar, and a pair of swinging jaws, substantially as described.

6. A supporting bed or table having a groove, *j*, combined with an endless apron or carrier, a removable bottomless holder, a pressure-bar, and a pair of swinging jaws, as set forth.

7. The jaws K, having the intersecting pivoted arms, in combination with the grooved bed and the removable bottomless holder.

8. In a machine for making cushions for finger-ring boxes, the receptacle O, having the sliding weighted bottom P′ and stops S S, combined with the table A, having suitable compressing and folding devices, substantially as described.

In testimony that I claim the foregoing I have hereunto set my hand and seal this 18th day of September, 1875.

BENJAMIN L. DENNISON. [L. S.]

Witnesses:

B. G. DENNISON,

WESTON THOMPSON.